US00PP19834P2

(12) United States Plant Patent
Zaiger et al.

(10) Patent No.: US PP19,834 P2
(45) Date of Patent: Mar. 17, 2009

(54) **INTERSPECIFIC *PRUNUS* TREE NAMED 'GYPZEE'**

(50) Latin Name: *Prunus species*
Varietal Denomination: Gypzee

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 12/069,890

(22) Filed: Feb. 14, 2008

(51) Int. Cl.
*A01H 5/00* (2006.01)

(52) U.S. Cl. ..... Plt./180

(58) Field of Classification Search ..... Plt./180
See application file for complete search history.

*Primary Examiner*—Annette H Para
*Assistant Examiner*—S. B. McCormick Ewoldt

(57) ABSTRACT

A new and distinct variety of interspecific tree. The following features of the tree and its fruit are characterized with the tree budded on 'Nemagaurd' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. The tree having a vigorous, upright growth habit.
2. Heavy and regular production of fruit.
3. Fruit with an attractive dark red skin color.
4. Fruit with a good balance between acid and sugar.
5. Fruit with very good flavor and eating quality.

1 Drawing Sheet

Botanical classification: *Prunus species.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific plum and apricot trees, which are known to us, and mentioned herein, are interspecific trees with proprietary identification numbers '321LH465', plumcot '4G720' and peachcot '10W100', 'King David' Plum (non-patented) and 'Flaming Gold' Apricot (U.S. Plant Pat. No. 2,822).

ORIGIN OF THE VARIETY

The new and distinct variety of interspecific tree, originated from multiple crosses of *Prunus salicina, Prunus armeniaca* and *Prunus persica,* was developed by us in our experimental orchard located near Modesto, Calif. It originated from seed of an open pollinated proprietary seedling with identification number '321LH465', which was developed by us from various crosses between 'King David' Plum (non-patented), 'Flaming Gold' Apricot (U.S. Plant Pat. No. 2,822) and the proprietary interspecific plumcot '4G720' and the proprietary peachcot '10W100'. A large group of these open pollinated seedlings were planted and grown on their own root system. Under close and careful observation, one such seedling, which is the present variety, exhibited desirable tree and fruit characteristics and in 1999 was selected for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The new interspecific variety [Plum ×(Plum×Plumcot)] ×[Plum×(Apricot×Peach)] is of large size, vigorous, upright growth and a productive and regular bearer of large, attractive dark red fruit, with very good flavor and eating quality. The fruit is further characterized by having firm yellow flesh, a good balance between acid and sugar, with an average Brix of 17.0°. In comparison to the proprietary seed parent '321LH465', the fruit is larger in size, having a dark red skin color, compared to blue and is approximately 10 days later in maturity. In comparison to the 'King David' Plum (non-patented), the fruit of the new variety is higher in Brix, more resistant to heat damage and approximately 8 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color.

Tree:

*Size.*—Large, pruned to approximately 3 to 3.5 meters in height for economical harvesting of fruit. Average width approximately 3 meters, varies with different cultural practices.

*Vigor.*—Vigorous, growth the first growing season of 1.5 to 2 meters, varies with fertility, type of soil and climatic conditions.

*Form.*—Upright, usually pruned to vase shape.

*Branching habit.*—Upright, crotch angle approximately 35°, increases with heavy production.

*Productivity.*—Productive, thinning and spacing of fruit necessary for desired market size.

*Bearer.*—Regular, adequate fruit set five consecutive years. No alternate bearing observed.

*Fertility.*—Self sterile, pollinator required.

*Density.*—Medium dense, usually pruned to vase shape to allow more sunlight to center of tree to improve new spur growth and enhance color of fruit.

*Hardiness.*—Hardy in all stone fruit growing areas of California. Winter chilling requirement approximately 900 hours at or below 45° F. Tree grown in USDA Hardiness Zone 9.

Trunk:

*Size.*—Large. Average circumference 55.8 cm, measured at 27.9 cm above ground on a 7 year old tree.

*Texture.*—Medium shaggy, increases with age.

*Color.*—Varies from 10YR 3/2 to 2.5Y 6/2.

Branches:

*Size.*—Medium. Average circumference 19.5 cm, measured at 1.1 meters above ground. Average crotch angle 35°, increases with heavy fruit production.

*Surface texture.*—New growth relatively smooth. Mature growth moderately rough, increases with age.

*Lenticels.*—Average number 41 in a 25.8 square cm surface. Average length 4.0 mm. Average width 2.0 mm. Color varies from 7.5YR 5/8 to 7.5YR 4/8.

*Color.*—New growth varies from 5GY 5/6 to 5GY 6/4. Mature growth varies from 2.5Y 5/2 to 2.5Y 3/2, varies with age of growth.

Leaves:

*Size.*—Medium. Average length 109.7 mm. Average width 48.9 mm.

*Form.*—Oblanceolate.

*Apex.*—Acuminate.

*Base.*—Cuneate.

*Margin.*—Serrate.

*Thickness.*—Medium.

*Surface texture.*—Upper surface relatively smooth, slight indentations over midrib and leaf veins, glabrous. Lower surface relatively smooth except for small ridges created by midrib and pinnate venation, glabrous.

*Petiole.*—Average length 15.7 mm. Average width 1.6 mm. Color varies from 5GY 7/4 to 5GY 6/4. Longitudinally grooved. Surface — very short pubescence.

*Glands.*—Type — globose. Size — medium. Average length 1.0 mm. Average diameter 0.6 mm. Average number 2. Located primarily on lower portion of leaf blade and upper portion of petiole. Color varies from 2.5GY 5/6 to 2.5GY 6/6.

*Color.*—Upper surface varies from 5GY 4/6 to 5GY 3/4. Lower surface varies from 5GY 4/2 to 5GY 4/4. Midvein color varies from 5GY 8/2 to 5GY 6/4.

Flower buds:

*Size.*—Small to medium. Average length 9.1 mm. Average diameter 5.1 mm.

*Hardiness.*—Hardy with respect to California winters.

*Form.*—Conical, becoming elongated just before opening.

*Pedicel.*—Average length 5.7 mm. Average width 0.8 mm. Surface — glabrous. Color varies from 2.5GY 7/8 to 5GY 7/6.

*Number of buds per spur.*—Average number 7, varies from 4 to 10.

*Color.*—N 9.5/ (white).

Flowers:

*Blooming period.*—Date of First Bloom Feb. 27, 2007. Date of Petal Fall Mar. 8, 2007, varies slightly with climatic conditions.

*Size.*—Small. Average height 9.4 mm. Average diameter 15.6 mm.

*Petals.*—Number 5, alternately arranged to sepals. Size — small. Average length 8.1 mm. Average width 6.2 mm. Form — elongated. Both upper and lower surfaces glabrous. Margin — sinuate. Color — N 9.5/ (white).

*Sepals.*—Number 5, alternately arranged to petals. Size — small. Average length 2.7 mm. Average width 2.2 mm. Shape — triangular. Margin — entire. Both upper and lower surfaces glabrous. Color — upper surface varies from 2.5GY 6/8 to SGY 6/6. Lower surface varies from 5GY 7/8 to 5GY 6/8.

*Stamens.*—Number — average 31 per flower. Filament length 8.5 mm. Filament color N 9.5/ (white). Anther color varies from 2.5YR 5/10 to 2.5YR 5/12.

*Pollen.*—Self sterile, pollinator required. Color varies from 5Y 8/10 to 5Y 7/10.

*Pistil.*—Normally one. Surface — glabrous. Average length 6.9 mm. Position of stigma — even with anthers. Color varies from 10Y 7/6 to 2.5GY 8/6.

*Fragrance.*—Moderate aroma.

*Color.*—N 9.5/ (white).

*Number flowers per flower bud.*—Average number 2, varies from 1 to 4.

*Pedicel.*—Average length 7.6 mm. Average width 0.7 mm. Color varies from 2.5GY 6/8 to 5GY 7/6. Surface — glabrous.

Fruit:

*Maturity when described.*—Firm ripe.

*Date of first picking.*—Aug. 1, 2007.

*Date of last picking.*—Aug. 8, 2007, varies slightly with climatic conditions.

*Size.*—Large. Average diameter axially 68.0 mm. Average transversely in suture plane 67.8 mm. Average weight 190.3 grams, varies slightly with fertility of the soil, amount of thinning and climatic conditions.

*Form.*—Globose to slightly elongated.
*Suture.*—Nearly smooth, extends from base to apex.
*Ventral surface.*—Nearly smooth, some fruit with very slight depression.
*Apex.*—Nearly rounded, some fruit slight tip.
*Base.*—Flat to slightly retuse.
*Cavity.*—Rounded to slightly elongated in suture plane. Average depth 1.5 mm. Average diameter 5.1 mm.

Stem:
*Size.*—Small. Average length 9.2 mm. Average diameter 3.0 mm.
*Colors.*—Varies from 2.5GY 5/6 to 5Y 4/6.

Flesh:
*Ripens.*—Evenly, only very slightly earlier near apex.
*Texture.*—Firm, meaty.
*Fibers.*—Few, small, tender.
*Firmness.*—Firm, will hold firm on the tree 10 days after maturity, shipping ripe.
*Aroma.*—Moderate.
*Amydgalin.*—Undetected.
*Eating quality.*—Very good.
*Flavor.*—Very good, good balance between acid and sugar.
*Juice.*—Moderate, enhances flavor.
*Brix.*—Average 17.0°, varies slightly with amount of fruit per tree and climatic conditions.
*Color.*—Varies from 5Y 9/6 to 5Y 8.5/6 with slight bleeding from skin 5R 4/10. Pit cavity color varies from 7.5YR 7/6 to 10YR 7/6.

Skin:
*Thickness.*—Medium.
*Surface.*—Smooth.
*Bloom.*—Moderate amount, completely covered.
*Tendency to crack.*—None.
*Color.*—Ground color varies from 2.5Y 9/4 to 2.5Y 8.5/6. Overspread with 2.5R 2/6. Very small, randomly spaced areas of ground color exposed to give a speckling pattern to surface areas.
*Tenacity.*—Tenacious to flesh.
*Astringency.*—Undetected.

Stone:
*Type.*—Clingstone.
*Size.*—Large. Average length 28.4 mm. Average width 21.1 mm. Average thickness 10.1 mm.
*Form.*—Ovoid.
*Base.*—Usually flat, some stones slightly rounded.
*Apex.*—Slightly pointed. Average length 3.5 mm.
*Surface.*—Slightly pitted throughout, one shallow groove on each side of suture, extending from base to apex.
*Sides.*—Unequal, one side extending further from suture plane.
*Ridges.*—Very small, narrow ridges extend from base toward apex.
*Tendency to split.*—None.
*Color.*—Varies from 7.5YR 5/6 to 10YR 5/8.

Kernel:
*Size.*—Medium. Average length 15.4 mm. Average width 9.6 mm. Average depth 4.7 mm.
*Form.*—Ovoid.
*Viability.*—Viable, complete embryo development.
*Skin.*—Color varies from 5Y 9/6 to 5Y 8/6 when dry.

Use: Dessert.
*Market.*—local and long distance.

Keeping quality: Good, held firm in cold storage 14 days at 38° to 42° without internal breakdown of flesh or appreciable loss of flavor.

Shipping quality: Good, minimal flesh bruising or skin scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of interspecific tree, substantially as illustrated and described, characterized by its large size, vigorous, upright growth and being a regular and productive bearer of large, firm, yellow flesh, clingstone fruit with very good flavor and eating quality; the fruit is further characterized by having an attractive red skin color, holding firm on the tree days after maturity (shipping ripe) a good balance between acid and sugar with an average Brix of 17.0°.

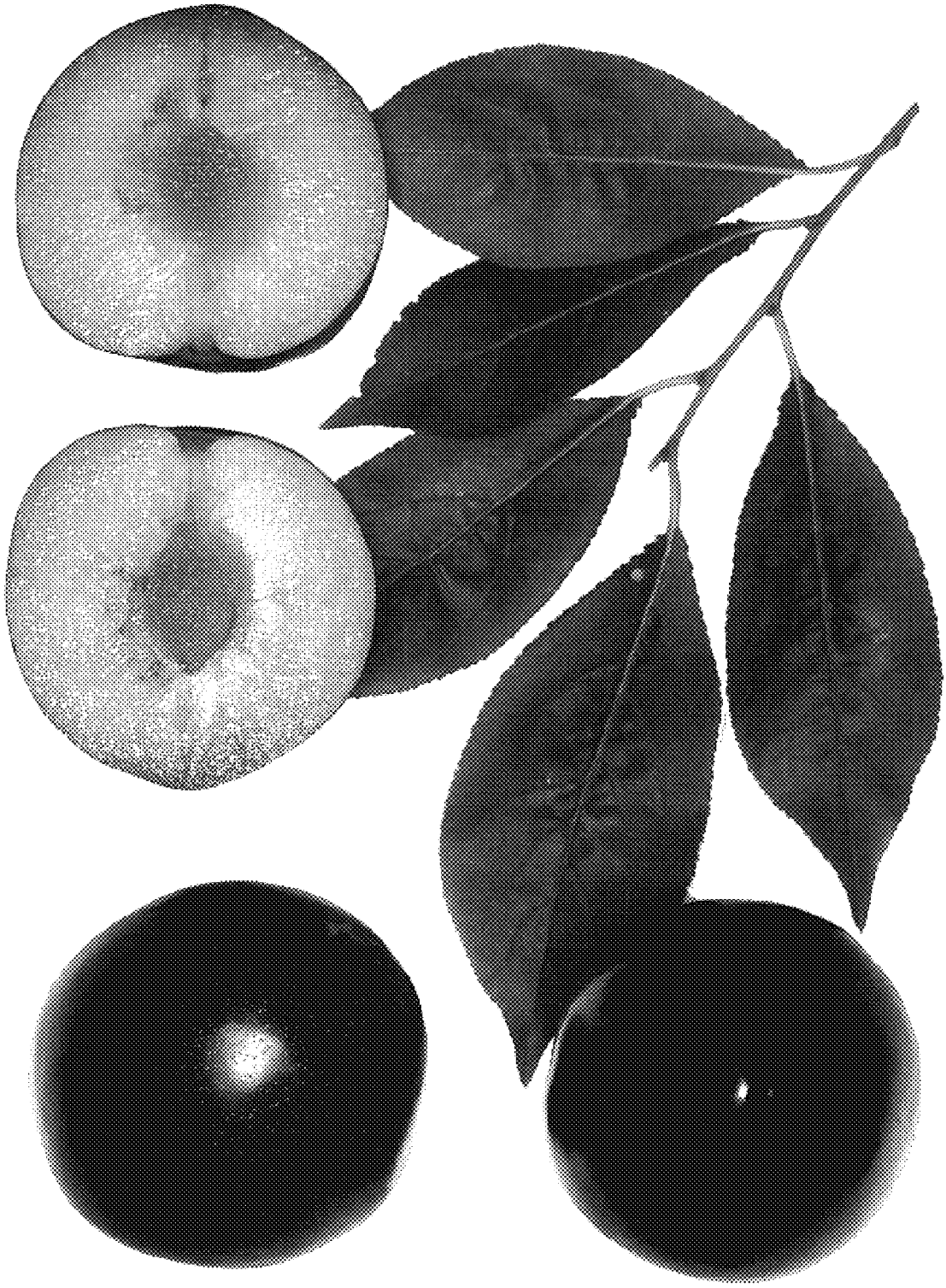

* * * * *